(12) United States Patent
Bastarda et al.

(10) Patent No.: US 8,309,719 B2
(45) Date of Patent: Nov. 13, 2012

(54) PROCESS FOR THE PREPARATION OF METHYL ESTER OF ROSUVASTATIN

(75) Inventors: Andrej Bastarda, Vrhnika (SI); Rok Grahek, Kranj (SI); Martin Crnugelj, Ljubljana (SI)

(73) Assignee: LEK Pharmaceuticals D.D., Ljubljana (SI)

( * ) Notice: Subject to any disclaimer, the term of this patent is extended or adjusted under 35 U.S.C. 154(b) by 309 days.

(21) Appl. No.: 12/672,119

(22) PCT Filed: Aug. 1, 2008

(86) PCT No.: PCT/EP2008/060125
§ 371 (c)(1),
(2), (4) Date: Feb. 4, 2010

(87) PCT Pub. No.: WO2009/019211
PCT Pub. Date: Feb. 12, 2009

(65) Prior Publication Data
US 2011/0184172 A1    Jul. 28, 2011

(30) Foreign Application Priority Data
Aug. 8, 2007    (EP) .................................... 07114009

(51) Int. Cl.
*C07D 239/02* (2006.01)
(52) U.S. Cl. ........................................................ 544/297
(58) Field of Classification Search ................... 544/297
See application file for complete search history.

(56) References Cited

U.S. PATENT DOCUMENTS 5,260,440 A * 11/1993 Hirai et al. .................... 544/332

FOREIGN PATENT DOCUMENTS

| EP | 0 521 471 B1 | 1/1993 |
|---|---|---|
| WO | WO 03/016317 A1 | 2/2003 |
| WO | WO 03/097614 A2 | 11/2003 |
| WO | WO 2005/042522 A1 | 5/2005 |
| WO | WO 2006/017357 A1 | 2/2006 |
| WO | WO 2007/000121 A1 | 1/2007 |

* cited by examiner

*Primary Examiner* — James O Wilson
*Assistant Examiner* — Ebenezer O Sackey
(74) *Attorney, Agent, or Firm* — Arent Fox LLP

(57) ABSTRACT

Process for the preparation of enantiomerically pure methyl ester of rosuvastatin has been developed, wherein the crude methyl ester ester is first purified by preparative chromatography, followed by crystallization.

5 Claims, 4 Drawing Sheets

PROCESS FOR THE PREPARATION OF METHYL ESTER OF ROSUVASTATIN

CROSS-REFERENCE TO RELATED APPLICATIONS

This application is a 371 National Stage entry of International Application No. PCT/EP2008/060125 filed Jan. 8, 2008, now WO 2009/019211 with an International Publication date of Feb. 12, 2009, which claims the benefit of EP 07114009.9 filed Aug. 8, 2007, the entire specification, claims and drawings of which are incorporated herewith by reference.

The present invention relates to a new process for the preparation of enantiomerically pure methyl ester of rosuvastatin (MER), which is used as HMG-CoA reductase inhibitor. The present invention also relates to crystalline MER. The present invention provides a new process for the preparation of chromatographically pure MER and enantiomerically pure MER.

BACKGROUND OF THE INVENTION

Rosuvastatin was first disclosed in EP 521471. This patent also disclosed a process for the preparation of rosuvastatin via methyl ester of rosuvastatin, methyl (E)-7-(4-(4-fluorophenyl)-6-isopropyl-2-(N-methylmethylsulfonamido)pyrimidin-5-yl)-3,5-dihydroxyhept-6-enoate, (thereon MER) which is one of the key intermediate in the synthesis of rosuvastatin. Processes for the preparation of rosuvastatin via MER are also disclosed in WO 03/016317, WO 03/097614, WO 06/017357. MER is described as "syrup" in the above mentioned publications. On the other hand, WO 05/042522 discloses crystalline ethyl, iso-propyl, tert-butyl esters of rosuvastatin.

While MER is converted to rosuvastatin salt in one (or two) step reaction, the purity of rosuvastatin is greatly affected by the purity of MER. Therefore, there is a need for developing improved process for the preparation of pure MER.

A "chromatographically pure methyl ester of rosuvastatin" in the present invention means chromatographically purified substance, obtained from collected fraction of eluent, containing substantially only MER, in other words: chromatographically pure substance is obtained by chromatography under conditions that a single peak, corresponding to that substance will be eluted and will substantially not overlap with peaks for other substances. In particular this will mean MER having less than 0.5% of substances different from 3S,5R, or 3R,5S of methyl ester of rosuvastatin.

An "enantiomerically pure MER" means MER containing more than 99% of 3R,5S eneantiomer, that is consequently less than 1% of 3S,5R, preferably less than 0.5% of 3S,5R, more preferably less than 0.1% of 3S,5R enantiomer. The % above refer to area.

It was found that MER can be obtained in crystalline form. It was especially surprising, that only a mixture of MER enantiomers is able to crystallize. Consequently, if a solution contains an excess of desired enantiomer, the mixture of enantiomers will crystallize, leaving only desired enantiomer in solution.

BRIEF SUMMARY OF THE INVENTION

Crude methyl ester of rosuvastatin may be prepared according known processes, e.g. process described in EP 521471. As thus prepared substance may contain diastereoisomeric impurities, as well as 3S,5R enantiomer, it is further purified by subjecting to preparative chromatography (in particular preparative HPLC). Such purification will yield chromatographically pure methyl ester of rosuvastatin. From the combined fractions, if methylcycohexane, isooctane, isopropanol, ethanol, methanol, ethylacetete, ethylmethylketone, tetrahydrofurane, in particular diisopropylether, is used for elution of MER, after optional concentration and cooling, methyl ester of rosuvastatin crystallizes. Thus crystallized mixture of MER enantiomers contains from 50 to 90% of 3R,5S enantiomer and from 10 to 50% of 3S,5R enantiomer.

In particular, the crude methyl ester of rosuvastatin will have an assay of about 70 to 75%, and chromatographic purity of about 80 to 85%, which will after purification be increased to 95 to 100%. Typically crude methyl ester of rosuvastatin will contain from 80 to 99% of 3R, 5S enantiomer and from 1 to 20% of 3S, 5R enantiomer, and the chromatographic purification does not affect this ratio.

Alternatively, MER having chromatographic purity above 87% may be dissolved in an etheric solvent, in particular diisopropyleteher or its mixture with isopropanol, and upon cooling and/or concentration the methyl ester of rosuvastatin as above crystallizes.

From the above solution of mixture of 3R,5S and 3S,5R enantiomer methyl ester of rosuvastatin crystallizes a mixture of enantiomer containing from 10 to 50% of 3S,5R enantiomer, while leaving in solution substantially only the desired 3R,5S enantiomer.

The desired enantiomerically pure MER may be isolated from solution and converted into rosuvastatin or its salt by methods known in the art, e.g. by hydrolysis with excess of NaOH, and trans-salification.

Figure 2:
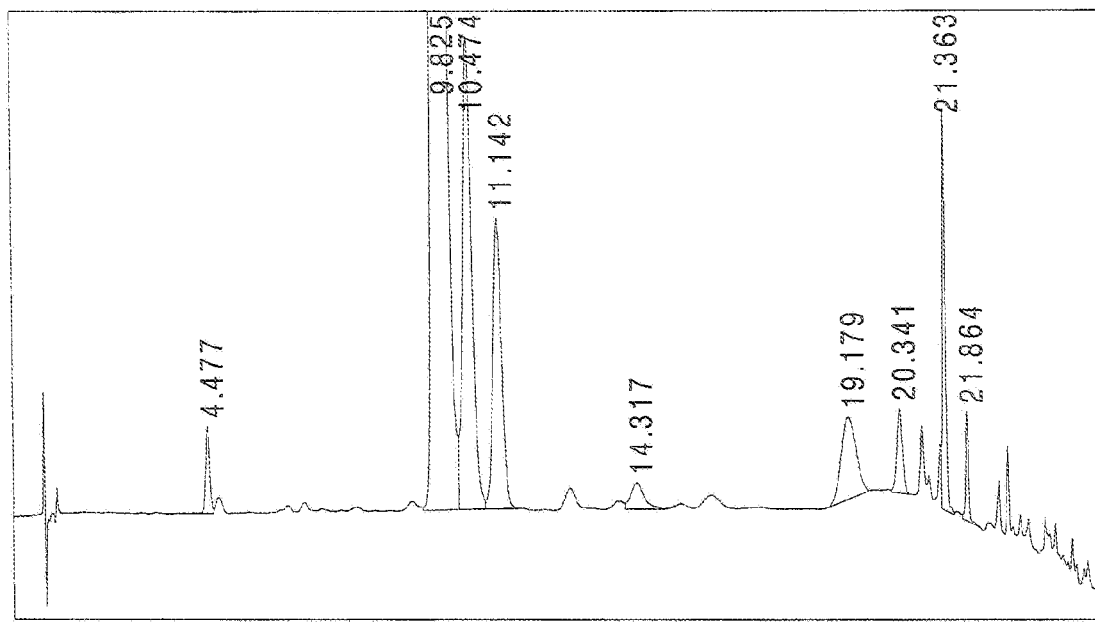
FIG. 2 is HPLC chromatogram of crude methyl ester of rosuvastatin, having about 87% chromatographic purity.
Figure 3:
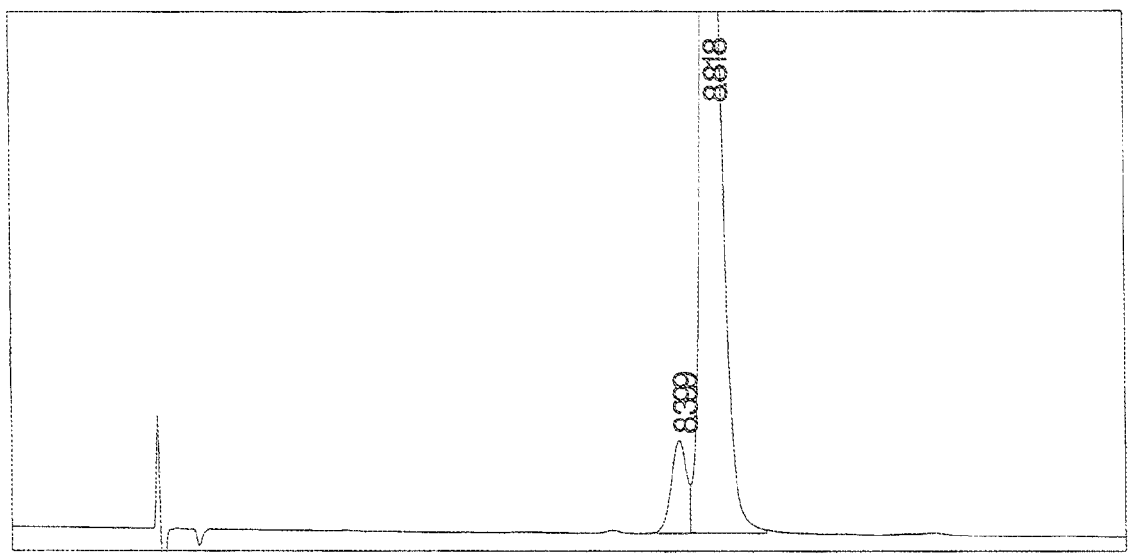
FIG. 3 is HPLC chromatogram of chromatographic pure methyl ester of rosuvastatin, having about 99.8% chromatographic purity, having about 93% enantiomeric purity.
Figure 4:
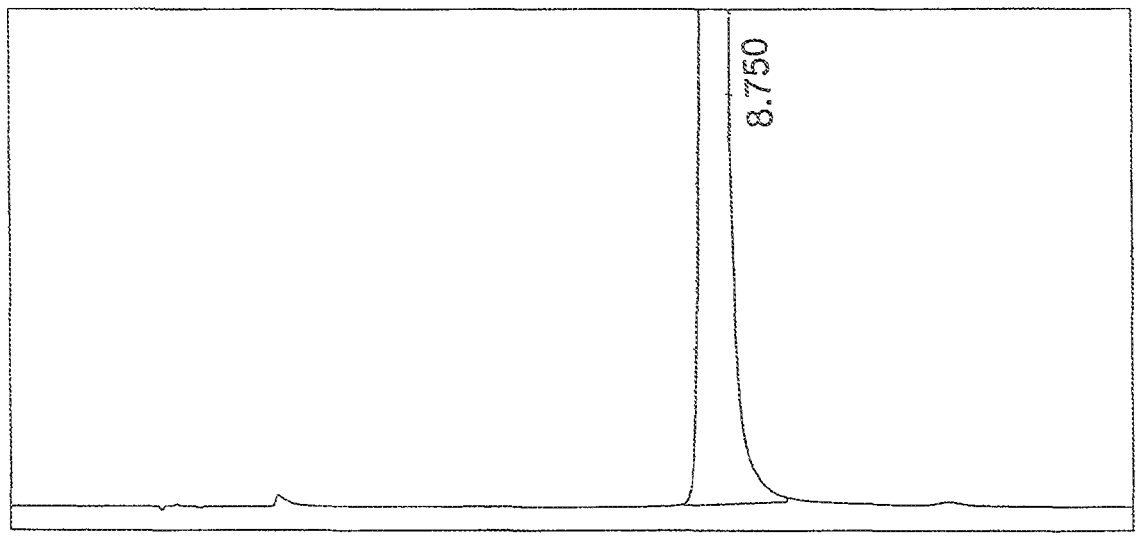
FIG. 4 is HPLC chromatogram of enantiomerically pure methyl ester of rosuvastatin, having about 99.9% enantiomeric purity.

(In the FIGS. 2 to 4 the ordinate represents the retention time, while abscissa represents the intensity.)

DETAILED DESCRIPTION OF THE INVENTION

A first object of the present invention is related to a process for the preparation of enantiomerically pure MER comprising the steps:
(a) purification of crude MER by (preparative) HPLC obtaining fractions comprising MER,
(b) crystallization of a mixture of MER enantiomers from fractions comprising MER,
(c) separation of a crystalline MER comprising a mixture of MER enantiomers obtained in step (b), preferably by filtration,
(d) obtaining a filtrate comprising enantiomerically pure MER,
(e) optionally, isolating of a solid enantiomerically pure MER.

In a particular process according to the present invention, step (a) comprises the following sub-steps of:

(a1) dissolving crude MER in diisopropyl ether (or an alternative solvent, suitably chosen based on the choice of mobile phase for chromatography)
(a2) loading a solution obtained in step a1) on a chromatographic column with porous silica gel, or an alternative stationary phase,
(a3) eluting a column with a mobile phase comprising a mixture of diisopropyl ether/isopropanol in a ratio from 85/15 to 99.5/0.5 (v/v), preferably 98.5/1.5 (v/v),
(a4) collecting fractions comprising MER.

In step (a2) any commercially available stationary phase comprising porous silica gel or diol or nitrile derivatized porous silica gel may be used. An example is Licospher 100, Lichrospher 100 Diol, Lichrospher 100 CN, LiChrosorb 60, Kromasil 100 Si, Kromasil 100 diol, Luna Si, Luna CN, etc.

In a particular process according to the present invention, step (b) comprises the following sub-steps of:
(b1) concentrating fractions comprising MER obtained in step (a) or (a4),
(b2) cooling a solution obtained in step (b1) to temperature from −40° C. to 0° C. for 1 hour to few days (3-5 days). The time needed for crystallization depends on the enantiomeric purity of the starting substance: purer it is, slower it crystallizes. Alternatively the substance of low enantiomeric purity may crystallize already at room temperature.

In particular, in step (b1) fractions comprising MER are concentrated by evaporation under reduced pressure.

In particular, a solution in step (b2) is cooled to −20° C. for 3 days.

Solid enantiomerically pure MER may be in a specific embodiment isolated in step (e) by drying under vacuum at temperature from 20 to 80° C. for 1 to 48 hours, more preferably at 40° C. for 5 hours Specifically the process for the preparation of enantiomerically pure MER according to the present invention comprising the steps of:
(a) dissolving crude MER in diisopropyl ether,
(b) loading a solution obtained in step a) on a chromatographic column with porous silica gel as stationary phase,
(c) eluting a column with a mobile phase comprising a mixture of diisopropyl ether/isopropanol in a ratio from 98.5/1.5 (v/v),
(d) collecting fractions comprising MER,
(e) concentrating fractions comprising MER,
(f) cooling a solution obtained in step e) at −20° C. for 3 days,
(g) separation of a crystalline MER comprising a mixture of MER enantiomers (racemic mixture of MER) by filtration,
(h) obtaining a filtrate comprising enantiomerically pure MER,
(i) optionally, obtaining a solid/dry enantiomerically pure MER.

Another object of the present invention is related to use of process for the preparation of enantiomerically pure MER according to the present invention for the preparation of enantiomerically pure rosuvastatin or its salts.

Figure 1:
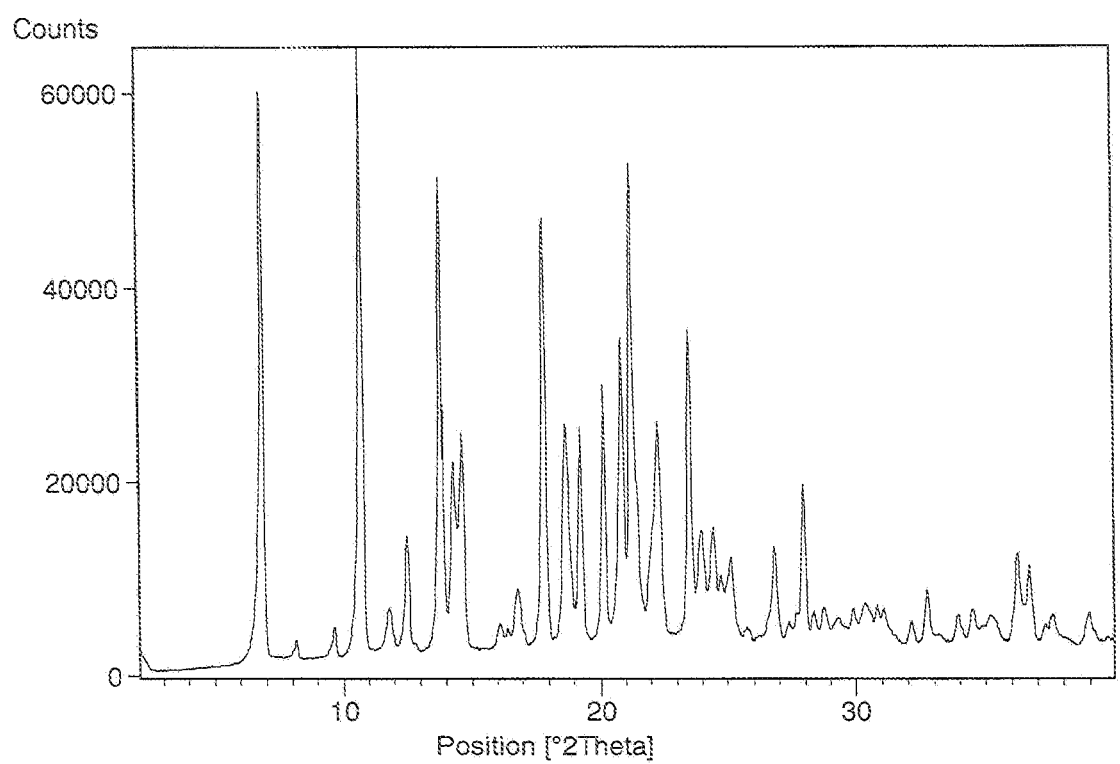
FIG. 1 is an XRPD pattern of crystalline methyl ester of rosuvastatin.

Another object of the present invention is related to crystalline MER. The crystallinity of MER is confirmed by X-ray powder diffraction (XRPD) pattern exhibiting distinctive peaks. Distinctive peaks will have half width below 1° 2θ. Crystalline MER may be characterized by a XRPD pattern comprising the following characteristic reflection angles 2θ: 6.9±0.2°, 10.8±0.2°, 13.9±0.2°, 17.9±0.2° and 21.3±0.2°. The XRPD pattern will be substantially similar to that on FIG. 1, which means that overall peak positions will be the same within ±0.2 or ±0.1 error margin, and the relative intensities will be similar. The exact peak positions depend on recording conditions, e.g. type of difractometer and algorithm to detect maxima used, while intensities will differ ±30% as a function of sample preparation (e.g. particle size and preferred orientation).

Crystalline MER may be further characterized by a powder x-ray diffraction pattern comprising the following characteristic reflection angles 2θ: 6.9±0.2°, 10.8±0.2°, 12.5±0.2°, 13.9±0.2°, 14.3±0.2°, 14.7±0.2°, 17.9±02°, 18.7±0.2°, 20.2±0.2°, 20.9±02°, 21.3±0.2°, 22.3±0.2° and 23.5±0.2°.

In particular an XRPD pattern of crystalline MER may be tabelated as follows:

| Position [° 2θ] | Rel. Int. [%] |
|---|---|
| 6.9 | 99 |
| 10.8 | 100 |
| 12.5 | 19 |
| 13.9 | 78 |
| 14.3 | 32 |
| 14.7 | 35 |
| 17.9 | 71 |
| 18.7 | 37 |
| 19.3 | 36 |
| 20.2 | 43 |
| 20.9 | 51 |
| 21.3 | 80 |
| 22.3 | 36 |

Another object of the present invention is related to a process for the preparation of crystalline MER comprising the steps (following providing a crude MER):
(a) purification of crude MER by (preparative) HPLC,
(b) crystallization of a mixture of MER enantiomers from fractions comprising MER,
(c) separation of a crystalline MER comprising a mixture of MER enantiomers obtained in step (b), preferably by filtration,
(d) optionally, drying of MER crystals.

A particular process for the preparation of crystalline MER according to the present invention comprising the steps of:
a) dissolving crude MER in diisopropyl ether,
b) loading a solution obtained in step a) on a chromatographic column with porous silica gel as stationary phase,
c) eluting a column with a mobile phase comprising a mixture of diisopropyl ether/isopropanol in a ratio 98.5/1.5 (v/v),
d) collecting a fraction comprising MER,
e) concentrating a fraction comprising MER,
f) cooling a solution obtained in step to temperature from −40° C. to 0° C.,
g) separation of a crystalline MER comprising a racemic mixture of MER, (which crystallized from solution upon cooling in previous step)
h) optionally, drying of MER crystals.

Another object of the present invention is related to use of crystalline MER comprising a mixture of MER enantiomers for the preparation of enantiomerically pure MER.

Another object of the present invention is related to use of crystalline MER comprising a mixture of MER enantiomers for the preparation of enantiomerically pure rosuvastatin or its salts.

The following examples are offered to illustrate aspects of the present invention. X-Ray powder diffractogram IS recorded with diffractometer X'Pert PRO MPD; CuKα radiation and it is understood that the intensity of the diffraction signals may vary as a function of particle size of the sample or orientation, and that diffractions recorded under different conditions, i.e. different difractometers may differ for as much as ±0.2 °2-theta, but preferably not more than ±0.1 °2-theta.

The purity as used in this specification is determined by HPLC and is defined as ratio of area of the substance being assessed and total area. In particular when referring to enantiomeric purity it is determined using following parameters:

| | |
|---|---|
| Column: | Chiralpak IB, 5 um, 150 × 4,6 mm |
| Mobile phase: | n-hexane/ethanol/TFA 91/9/0,1 (V/V/V) |
| Flow rate: | 1.0 ml/min |
| Sample: | 10 mg/ml in acetonitrile |
| Injection volume: | 0.5 ul |
| Detector: | UV, 242 nm; |

(such analysis is presented in FIGS. 3 and 4)
while when referring to chromatographic purity it is determined using following parameters:

| | |
|---|---|
| Column: | Xbridge C18 3,5um, 150 × 4,6 mm |
| Mobile phase A: | 10 mM ammonium acetate pH 4.0/ACN/THF 70/25/5 |
| Mobile phase B: | 10 mM ammonium acetate pH 4.0/ACN/THF 25/70/5 |
| Gradient: | up to 19 min 90% A, 10% B; after 19 min 100% B) |
| Flow rate: | 2.2 ml/min |
| Sample: | 1 mg/ml in acetonitrile |
| Injection volumen: | 5 ul |
| Detector: | UV, 242 nm |

(such analysis is presented in FIG. 2):

The assay of the methyl ester of rosuvastatin may be determined chromatographically compared to standard.

Following representative examples further explain the invention:

Preparative HPLC

Chromatographic column: LiChrospher 100 DIOL 10 μm 250×20 mm

| | |
|---|---|
| Mobile phase A: | diisopropyl ether (DIPE) |
| Mobile phase B: | 1.5% isopropanol, 98.5% DIPE |
| Flow rate: | 60 ml/min |
| Detection: | UV, 345 nm |
| Injection volume: | 60 ml |

1.5 g of the crude sample (assay 70%) is dissolved in 60 ml of diisopropylether. The obtained solution is loaded on a chromatographic column, previously conditioned with mobile phase A. After the sample load the chromatographic column is eluted with mobile phase B. A central portion (ca 100 ml) of main peak is collected. The obtained fraction is pure MER, with ca 99.8% chromatographic purity, and ca 6-7% of enantiomer, as shown on FIG. 3.

Crystallization:

The fraction obtained in preparative HPLC is evaporated under reduced pressure (ca 200 mbar) to 50 ml and cooled in freezer (ca −20° C.) for 3 days. The suspension is filtered. The obtained crystals are dried under vacuum at 40° C. for 5 hours yielding 0.57 g of dry product, containing ca 11% of enantiomer.

Recovery of methyl(3R,5S,E)-7-(4-(4-fluorophenyl)-6-isopropyl-2-(N-methylmethylsulfonamido)pyrimidin-5-yl)-3,5-dihydroxyhept-6-enoate The filtrate of previous step is evaporated under reduced pressure and dried under vacuum at 40° C. for 5 hours yielding 0.43 g of dry product, containing less than 0.1% of 3S,5R enantiomer. The product is enantiomerically pure MER having 99.9% enantiomeric purity, shown on FIG. 4.

The invention claimed is:

1. A process for the preparation of enantiomerically pure methyl (3R,5S,E)-7-(4-(4-fluorophenyl)-6-isopropyl-2-(N-methylmethylsulfonamido)pyrimidin-5-yl)-3,5-dihydroxyhept-6-enoate (MER) comprising the steps of:
    a) purification of crude MER by HPLC,
    b) crystallization of a mixture of MER enantiomers from fractions comprising MER,
    c) separation of the crystallized mixture of MER enantiomers obtained in step (b), by filtration,
    d) obtaining a filtrate comprising enantiomerically pure MER, and
    e) optionally, isolation of a solid enantiomerically pure MER.

2. A process for the preparation of enantiomerically pure methyl (3R,5S,E)-7-(4-(4-fluorophenyl)-6-isopropyl-2-(N-methylmethylsulfonamido)pyrimidin-5-yl)-3,5-dihydroxyhept-6-enoate (MER) comprising the steps of:
    a) dissolving crude MER in diisopropyl ether,
    b) loading a solution obtained in step a) on a chromatographic column with porous silica gel as stationary phase,
    c) eluting a column with a mobile phase comprising a mixture of diisopropyl ether/isopropanol in a ratio from 98.5/1.5 (v/v),
    d) collecting fractions comprising MER,
    e) concentrating fractions comprising MER,
    f) cooling a solution obtained in step e) at −20° C. for 3 days,
    g) separation of a crystalline MER comprising a racemic mixture of MER enantiomers by filtration,
    h) obtaining a filtrate comprising enantiomerically pure MER, and
    i) optionally, obtaining a solid/dry enantiomerically pure MER.

3. A process for the preparation of crystalline methyl ester of rosuvastatin (MER) comprising the steps:
    a) purification of crude MER by HPLC,
    b) crystallization of a mixture of MER enantiomers from fractions comprising MER,
    c) separation of a crystalline MER comprising a mixture of MER enantiomers obtained in step (b), and
    d) optionally, drying of MER crystals.

4. A process for the preparation of crystalline methyl ester of rosuvastatin (MER) comprising the steps of:
    a) dissolving crude MER in diisopropyl ether,
    b) loading a solution obtained in step a) on a chromatographic column with porous silica gel as stationary phase,
    c) eluting a column with a mobile phase comprising a mixture of diisopropyl ether/isopropanol in a ratio 98.5/1.5 (v/v),
    d) collecting at least one fraction comprising MER,
    e) concentrating said at least one fraction comprising MER,
    f) cooling a solution obtained in previous step to temperature from −40° C. to 0° C., g) separating crystalline MER comprising a racemic mixture of MER, and h) optionally, drying crystalline MER.

5. A process for separation of methyl (3R,5S,E)-7-(4-(4-fluorophenyl)-6-isopropyl-2-(N-methylmethylsulfonamido)pyrimidin-5-yl)-3,5-dihydroxyhept-6-enoate from mixture of 3R,5S and 3S,5R enantiomers containing excess of 3R,5S enantiomers characterized by crystallizing a mixture of 3R,5S and 3S,5R enantiomers while leaving in solution the 3R, 5S enantiomer.

* * * * *